(12) United States Patent
Speeg et al.

(10) Patent No.: US 9,421,001 B2
(45) Date of Patent: *Aug. 23, 2016

(54) BIOPSY DEVICE TISSUE SAMPLE HOLDER WITH FLOW RESTRICTION DEVICE

(71) Applicant: Devicor Medical Products, Inc., Cincinnati, OH (US)

(72) Inventors: Trevor W. V. Speeg, Williamsburg, OH (US); John A. Hibner, Mason, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/461,580

(22) Filed: Aug. 18, 2014

(65) Prior Publication Data

US 2014/0358027 A1    Dec. 4, 2014

Related U.S. Application Data

(63) Continuation of application No. 12/707,712, filed on Feb. 18, 2010, now Pat. No. 8,845,546.

(51) Int. Cl.
*A61B 10/02* (2006.01)
*A61B 10/00* (2006.01)

(52) U.S. Cl.
CPC ......... *A61B 10/0096* (2013.01); *A61B 10/0266* (2013.01); *A61B 10/0275* (2013.01); *A61B 10/0283* (2013.01); *A61B 2010/0208* (2013.01); *A61B 2010/0225* (2013.01)

(58) Field of Classification Search
CPC ........... A61B 10/0096; A61B 10/0266; A61B 10/0275; A61B 10/0283; A61B 2010/0208; A61B 2010/0225

USPC ......................................... 600/562, 564–566
See application file for complete search history.

(56) References Cited

U.S. PATENT DOCUMENTS

| | | |
|---|---|---|
| 2,522,108 A | 9/1950 | Flagg |
| 5,526,822 A | 6/1996 | Burbank et al. |
| 6,086,544 A | 7/2000 | Hibner et al. |
| 6,485,436 B1 | 11/2002 | Truckai et al. |
| 6,626,849 B2 | 9/2003 | Huitema et al. |

(Continued)

FOREIGN PATENT DOCUMENTS

| | | |
|---|---|---|
| EP | 1642534 A2 | 4/2006 |
| WO | WO 98/33436 | 8/1998 |
| WO | WO 00/30531 | 6/2000 |

*Primary Examiner* — Lee S Cohen
*Assistant Examiner* — Emily Lloyd
(74) *Attorney, Agent, or Firm* — Frost Brown Todd LLC

(57) ABSTRACT

A tissue sample holder for a biopsy device comprises an outer cup, a collection tray, and a flow restriction device. The outer cup defines a hollow interior. The collection tray separates the hollow interior into an upper chamber and a lower chamber while allowing fluid to pass between the two chambers through an opening in the collection tray. The flow restriction device selectively seals the opening thereby preventing fluid from passing from the lower chamber into the upper chamber. The flow restriction device may be operable to selectively seal the opening in response to a vacuum being induced within the upper chamber. The collection tray may have a shape (e.g., tapered, funnel-shaped, convex, etc.) selected to facilitate the flow of fluid toward the opening. The lower chamber may be coupled with an external fluid collection device. The lower chamber may define a larger volume than the upper chamber.

20 Claims, 10 Drawing Sheets

(56) References Cited

U.S. PATENT DOCUMENTS

| | | |
|---|---|---|
| 7,442,171 B2 | 10/2008 | Stephens et al. |
| 7,854,706 B2 | 12/2010 | Hibner |
| 7,918,804 B2 | 4/2011 | Monson et al. |
| 8,083,687 B2 | 12/2011 | Parihar |
| 8,206,316 B2 | 6/2012 | Hibner et al. |
| 8,251,916 B2 | 8/2012 | Speeg et al. |
| 8,622,927 B2 | 1/2014 | Parihar et al. |
| 8,702,623 B2 | 4/2014 | Parihar et al. |
| 8,845,546 B2 * | 9/2014 | Speeg et al. .......... 600/565 |
| 2006/0074345 A1 | 4/2006 | Hibner |
| 2008/0214955 A1 | 9/2008 | Speeg et al. |
| 2010/0152610 A1 | 6/2010 | Parihar et al. |
| 2010/0160819 A1 | 6/2010 | Parihar et al. |

* cited by examiner

BIOPSY DEVICE TISSUE SAMPLE HOLDER WITH FLOW RESTRICTION DEVICE

This application is a continuation of U.S. patent application Ser. No. 12/707,712, published as U.S. Patent Application Pub. No. 2011/0201964, now U.S. Pat. No. 8,845,546, entitled "Biopsy Device Tissue Sample Holder with Flow Restriction Device," filed Feb. 18, 2010, the disclosure of which is incorporated by reference herein.

BACKGROUND

Biopsy samples have been obtained in a variety of ways in various medical procedures using a variety of devices. Biopsy devices may be used under stereotactic guidance, ultrasound guidance, magnetic residence imaging (MRI) guidance, positron emission mammography (PEM) guidance, breast specific gamma imaging (BSGI) guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Merely exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003; U.S. Pub. No. 2006/0074345, entitled "Biopsy Apparatus and Method," published Apr. 6, 2006; U.S. Pub. No. 2007/0118048, entitled "Remote Thumbwheel for a Surgical Biopsy Device," published May 24, 2007; U.S. Pub. No. 2008/0214955, entitled "Presentation of Biopsy Sample by Biopsy Device," published Sep. 4, 2008; U.S. Pub. No. 2009/0171242, entitled "Clutch and Valving System for Tetherless Biopsy Device," published Jul. 2, 2009; U.S. Non-Provisional patent application Ser. No. 12/335,578, entitled "Hand Actuated Tetherless Biopsy Device with Pistol Grip," filed Dec. 16, 2008; U.S. Non-Provisional patent application Ser. No. 12/337,942, entitled "Biopsy Device with Central Thumbwheel," filed Dec. 18, 2008; and U.S. Non-Provisional patent application Ser. No. 12/483,305, entitled "Tetherless Biopsy Device with Reusable Portion," filed Jun. 12, 2009. The disclosure of each of the above-cited U.S. patents, U.S. patent application Publications, and U.S. Non-Provisional patent applications is incorporated by reference herein.

While several systems and methods have been made and used for obtaining a biopsy sample, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
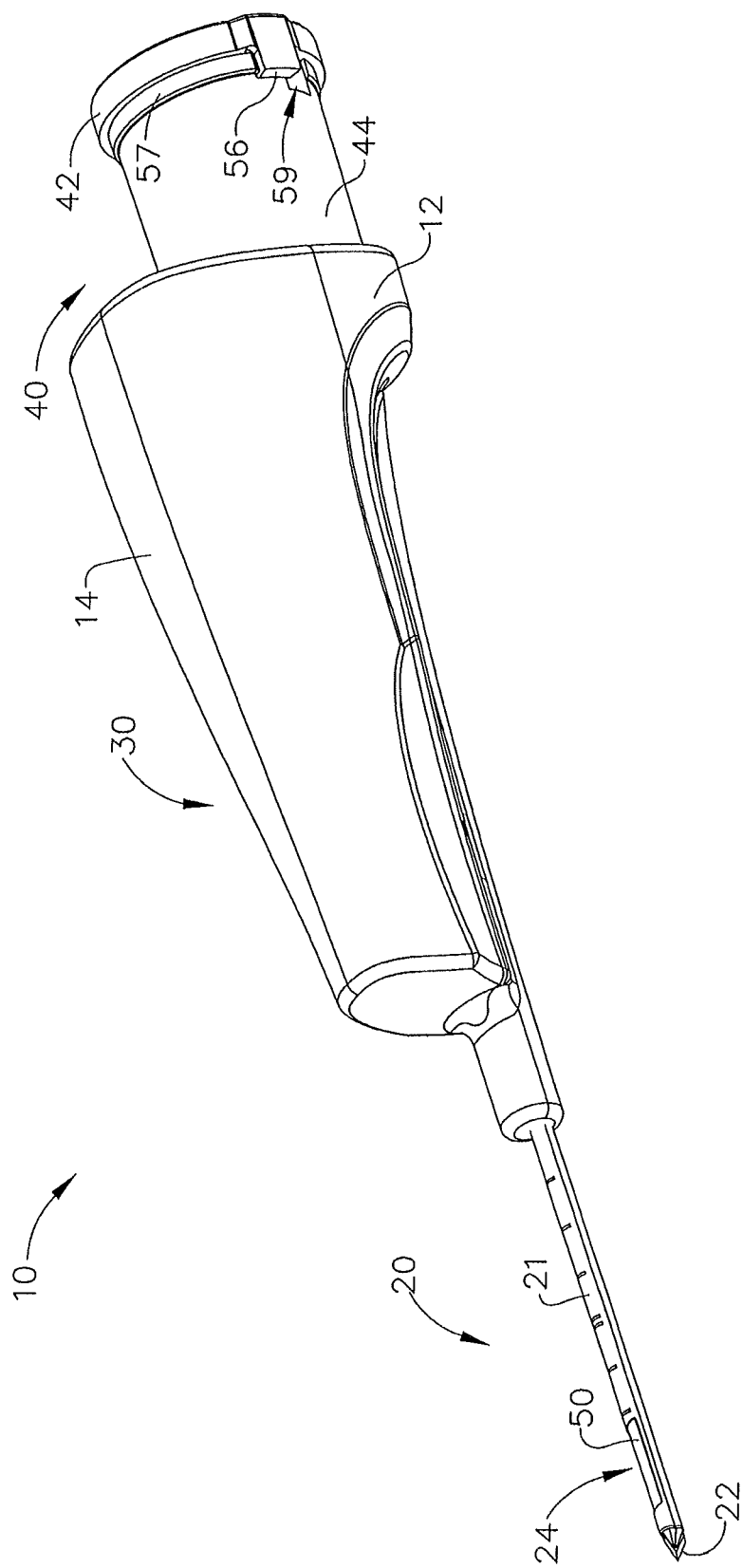
FIG. 1 depicts a perspective view of an exemplary biopsy device.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Overview

Figure 2:
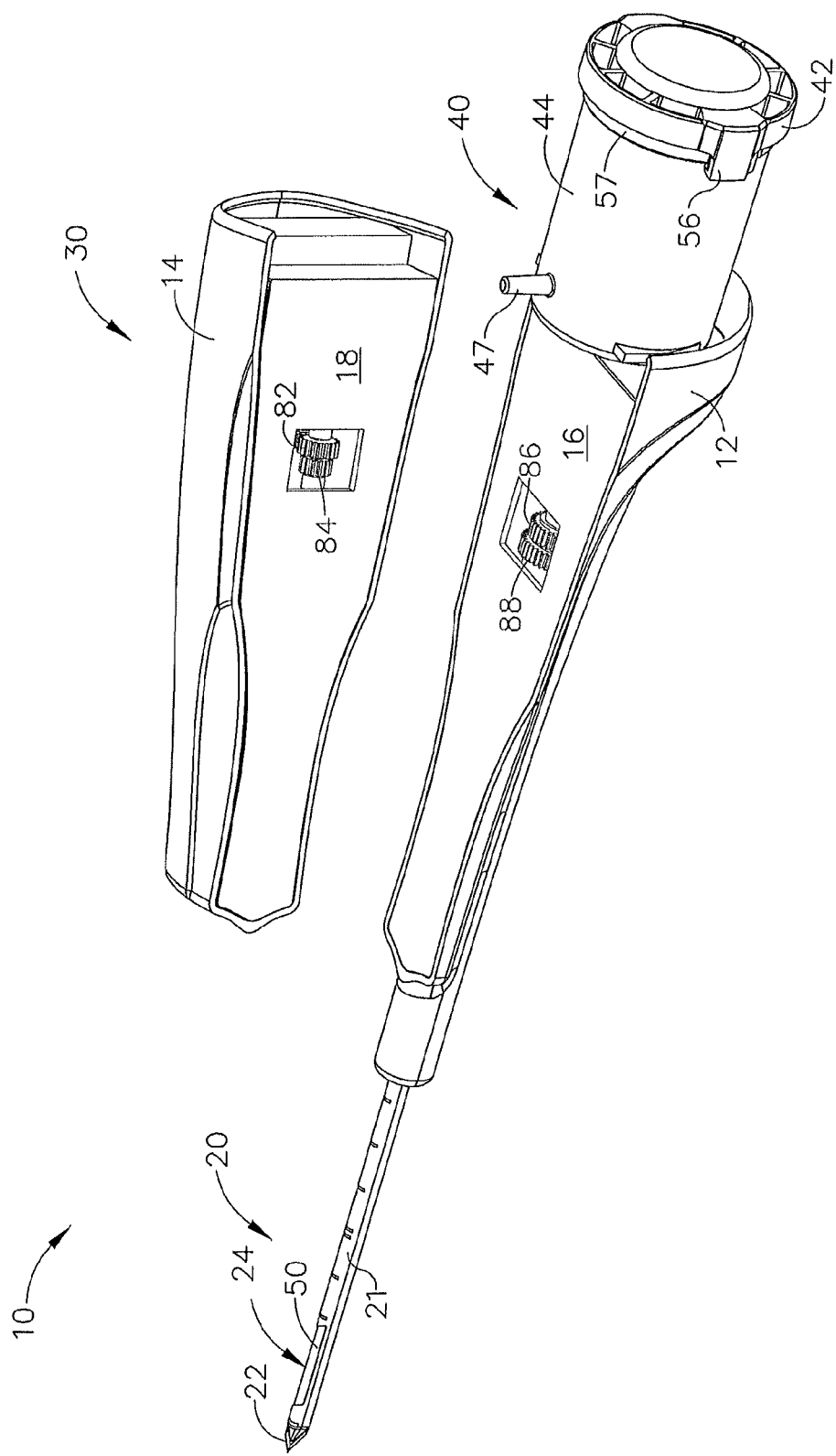
FIG. 2 depicts a perspective view of the biopsy device of FIG. 1, with a probe portion separated from a holster portion.
Figure 3:
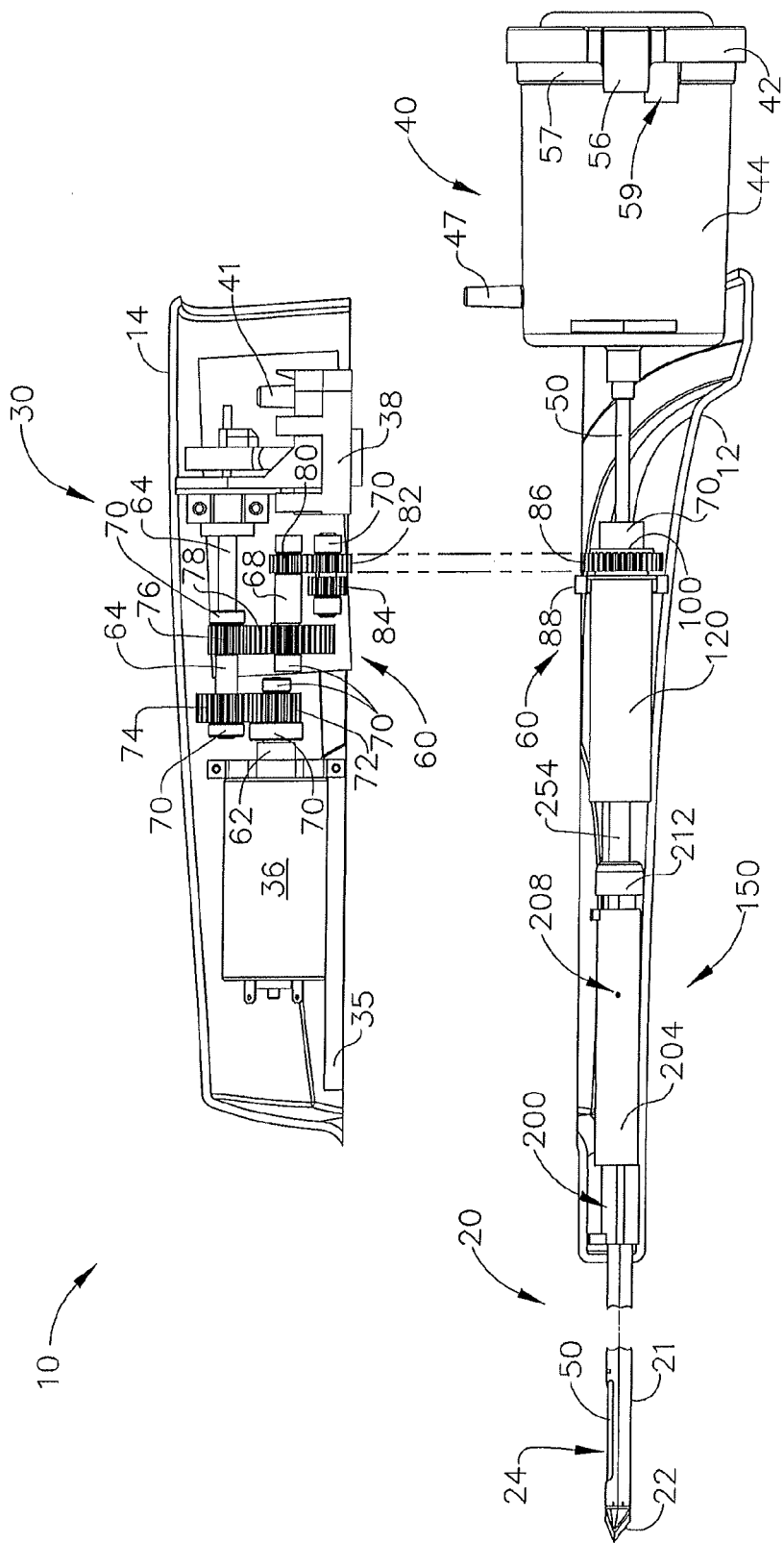
FIG. 3 depicts a side cross-sectional view of the biopsy device of FIG. 1, with the probe portion separated from the holster portion.

As shown in FIGS. 1-3, an exemplary biopsy device (10) comprises a needle (20), a body (30), and a tissue sample holder (40). In particular, needle (20) extends distally from the distal portion of body (30), while tissue sample holder (40) extends proximally from the proximal portion of body (30). Body (30) is sized and configured such that biopsy device (10) may be operated by a single hand of a user. In particular, and as described in greater detail below, a user may grasp body (30) with a single hand, insert needle (20) into a patient's breast, and collect one or a plurality of tissue samples from within the patient's breast, all with just using a single hand. Alternatively, a user may grasp body (30) with more than one hand and/or with any desired assistance. In some settings, the user may capture a plurality of tissue samples with just a single insertion of needle (20) in the patient's breast. Such tissue samples may be pneumatically deposited in tissue sample holder (40), as described in greater detail below, then retrieved from tissue sample holder (40) for analysis.

Body (30) of the present example comprises a probe (12) and a holster (14). As shown in FIGS. 2-3, and as described in greater detail below, probe (12) is separable from holster (14). In particular, probe (12) and holster (14) may be removably coupled using bayonet mounts (not shown) or any other suitable structures or features. Use of the term "holster" herein should not be read as requiring any portion of probe (12) to be inserted into any portion of holster (14). Indeed, in some variations of biopsy device (10), probe (12) may simply sit on holster (14). In some other variations, a portion of holster (14) may be inserted into probe (12). Furthermore, in some biopsy devices (10), probe (12) and holster (14) may be of unitary or integral construction, such that the two components cannot be separated. By way of example only, in versions where probe (12) and holster (14) are provided as separable components, probe (12) may be provided as a disposable component, while holster (14) may be provided as a reusable component. Still other suitable structural and functional relationships between probe (12) and holster (14) will be apparent to those of ordinary skill in the art in view of the teachings herein.

Some variations of biopsy device (10) may include one or more sensors (not shown), in probe (12) and/or in holster (14), that is/are configured to detect when probe (12) is coupled with holster (14). Such sensors or other features may further be configured to permit only certain types of probes (12) and holsters (14) to be coupled together. In addition or in the alternative, such sensors may be configured to disable one or more functions of probes (12) and/or holsters (14) until a suitable probe (12) and holster (14) are coupled together. Of course, such sensors and features may be varied or omitted as desired.

While examples described herein refer to the acquisition of biopsy samples from a patient's breast, it should be understood that biopsy device (10) may be used in a variety of other procedures for a variety of other purposes and in a variety of other parts of a patient's anatomy.

Exemplary Needle

As shown in FIGS. 1-6, needle (20) of the present example comprises a cannula (21) with a tissue piercing tip (22), a lateral aperture (24), a first lumen (26), and a second lumen (28). Tissue piercing tip (22) is configured to pierce and penetrate tissue, without requiring a high amount of force, and without requiring an opening to be pre-formed in the tissue prior to insertion of tip (22). A cutter (50) is disposed in first lumen (26), and is operable to rotate and translate within first lumen (26) as will be described in greater detail below. Lateral aperture (24) is located proximal to tip (22), is in fluid communication with first lumen (26), and is configured to receive tissue when needle (20) is inserted in a breast and when a cutter (50) is retracted as will also be described in greater detail below. A plurality of openings (27) may provide fluid communication between first and second lumens (26, 28). A plurality of external openings (not shown) may also be formed in needle (20), and may be in fluid communication with second lumen (28). Examples of such external openings are disclosed in U.S. Pub. No. 2007/0032742, entitled "Biopsy Device with Vacuum Assisted Bleeding Control," published Feb. 8, 2007, the disclosure of which is incorporated by reference herein. Of course, as with other components described herein, such external openings are merely optional.

Needle (20) of the present example further comprises a hub (200), as shown in FIGS. 3-6. Hub (200) may be formed of plastic that is overmolded about needle (20) or otherwise secured to needle (20), such that hub (200) is unitarily secured to needle (20). Alternatively, hub (200) may be formed of any other suitable material through any suitable process and may have any other suitable relationship with needle (20).

Figure 4:
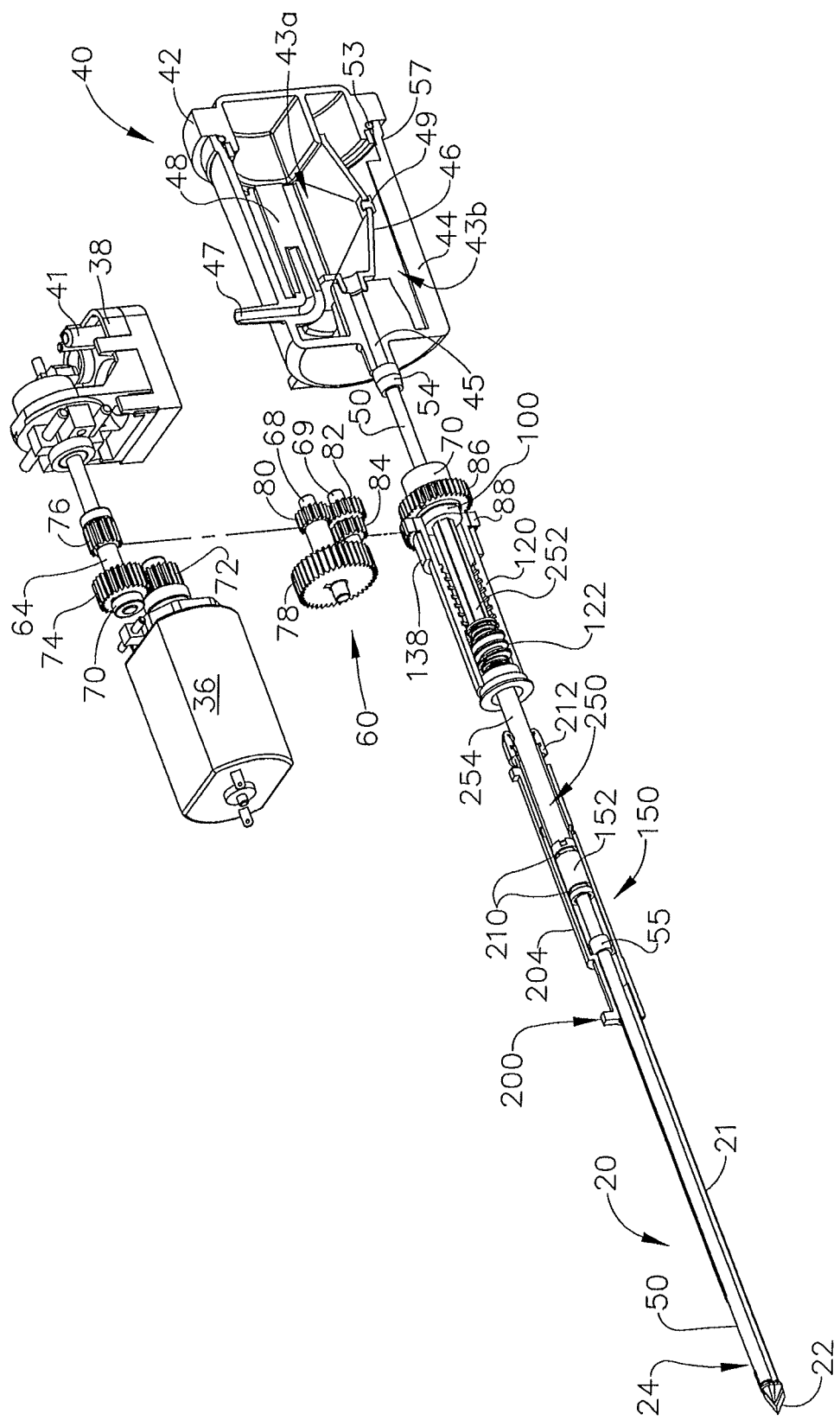
FIG. 4 depicts an exploded view of the biopsy device components of FIG. 3, with portions shown in cross-section.
Figure 5:
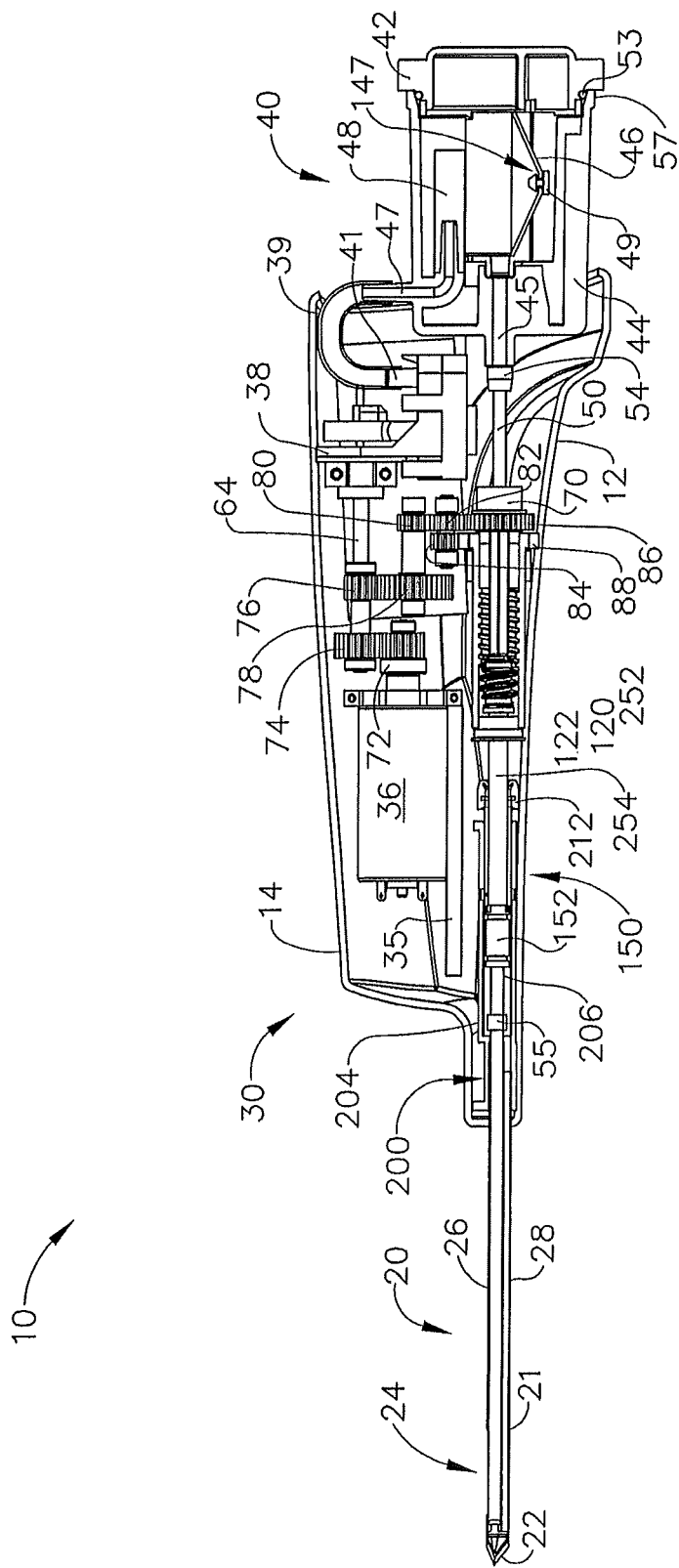
FIG. 5 depicts a side cross-sectional view of the biopsy device of FIG. 1.
Figure 6:
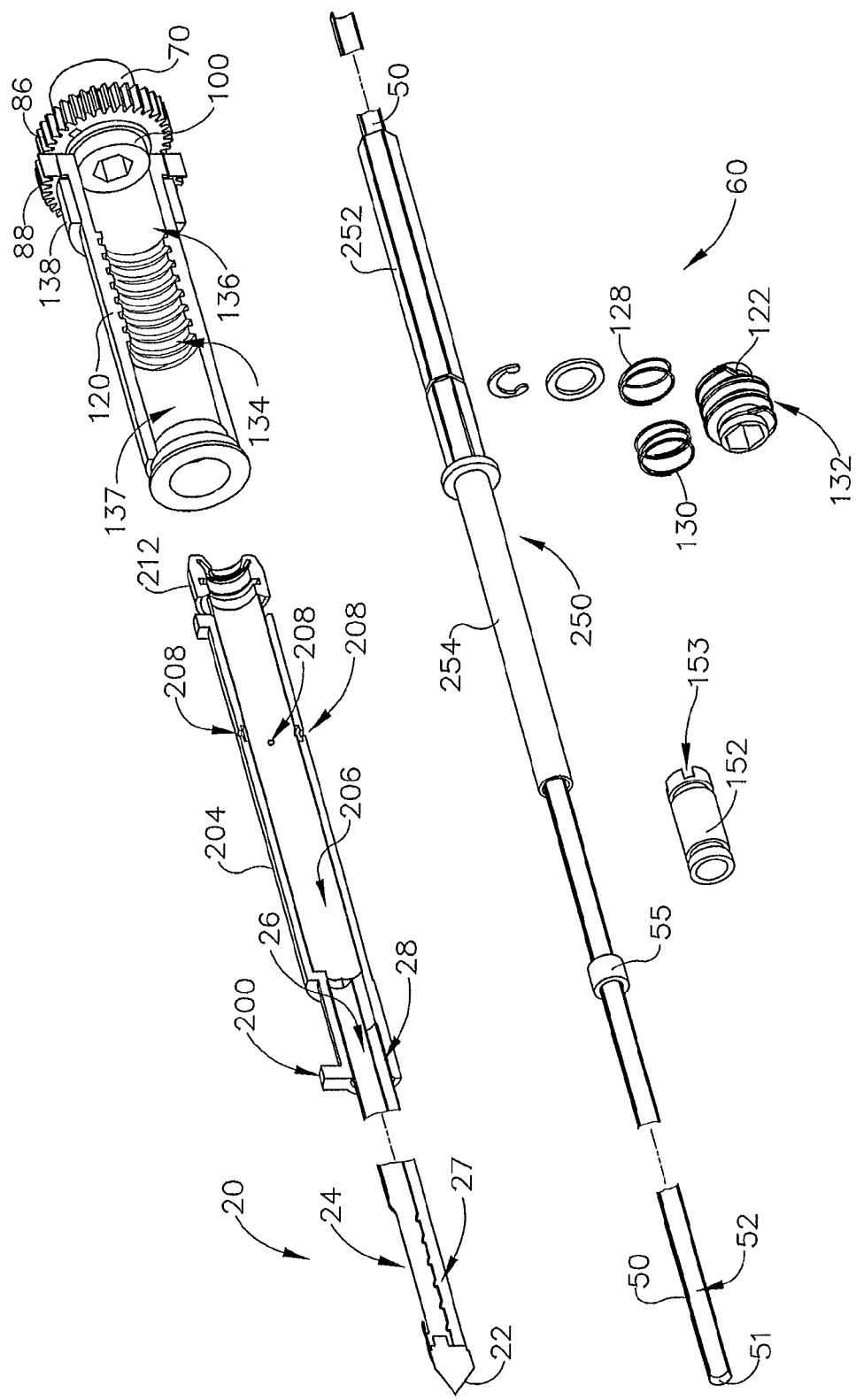
FIG. 6 depicts an exploded view of cutter and needle components of the biopsy device of FIG. 1, with portions shown in cross-section.
Figure 7:
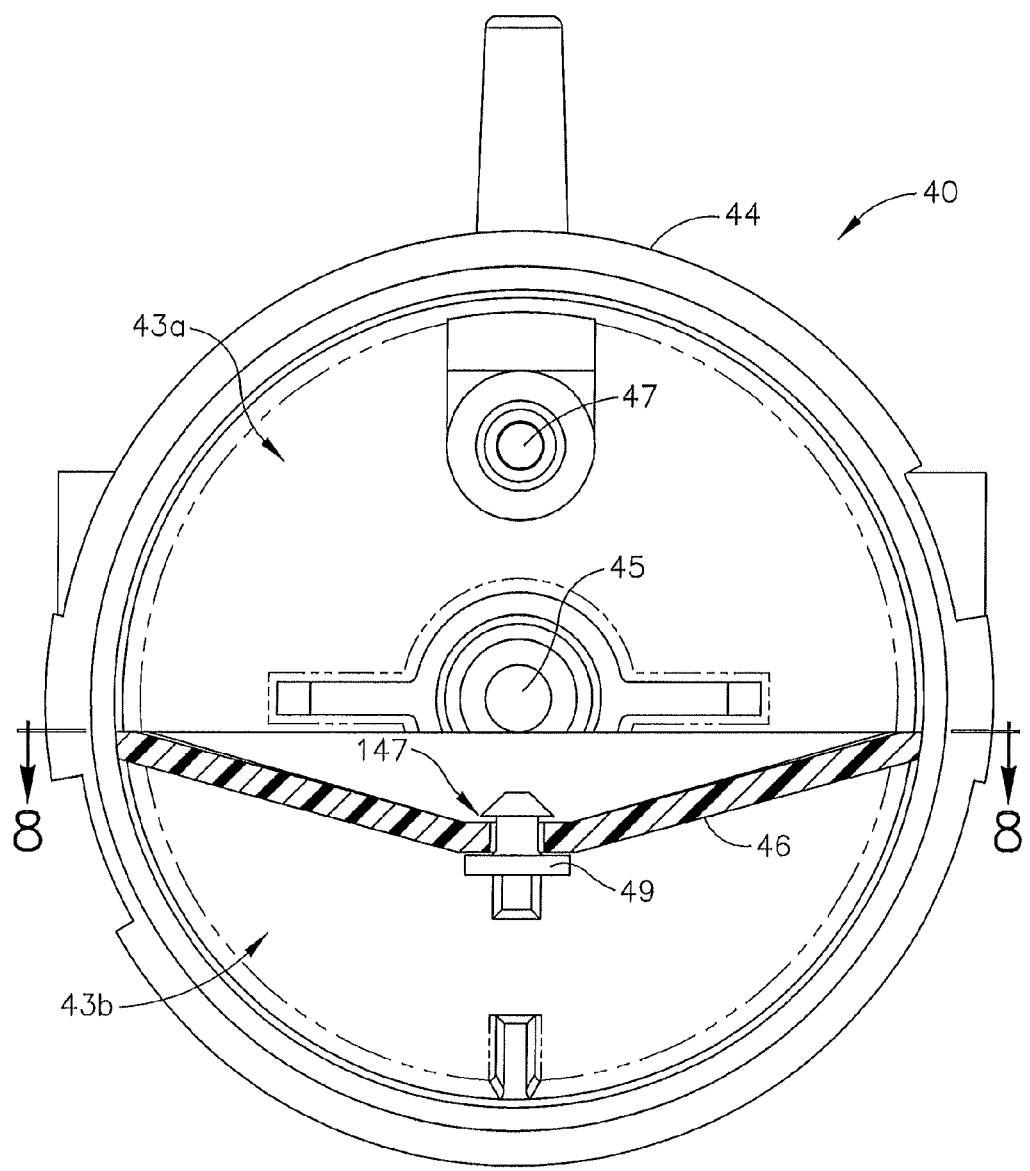
FIG. 7 depicts a rear cross-sectional view of an exemplary tissue sample holder with a flow restriction device.
Figure 8:
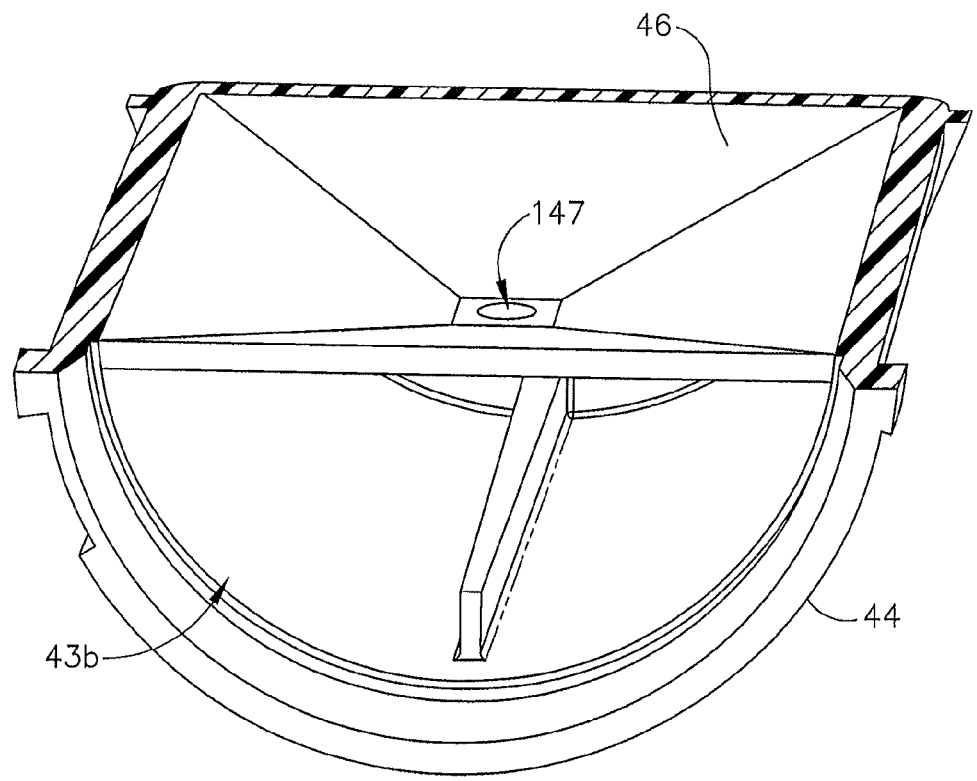
FIG. 8 depicts a rear, perspective cross-sectional view of the tissue sample holder of FIG. 7, with the flow restriction device removed.

Hub (200) of the present example comprises a sleeve portion (204). Sleeve portion (204) extends integrally into probe portion (12) of body (30). As shown in FIGS. 3-5, sleeve portion (204) defines a hollow interior (206), which is in fluid communication with second lumen (28) of needle (20). Sleeve portion (204) also defines a plurality of openings (208), which are radially spaced about the perimeter of sleeve portion (204) at a common longitudinal position, and which are in fluid communication with hollow interior (206). Openings (208) are exposed to ambient air, such that openings (208) provide a vent in the present example. Openings (208) are selectively fluidly coupled with second lumen (28) of needle (20) in this example, as will be described in greater detail below. In particular, openings (208) are selectively coupled with second lumen (28) during use of biopsy device (10), to selectively provide venting to second lumen (28). A pair of o-rings (210) are positioned about a shuttle valve slider (152), to substantially seal second lumen (28) relative to openings (208) when second lumen (28) is not to be vented, depending on the longitudinal position of slider (152) as will be described in greater detail below. A seal (212) is also provided at the proximal end of sleeve (204), at the interface of cutter (50) and sleeve (204). Seal (212) is configured to substantially seal the interface of cutter (50) and sleeve (204), even as cutter (50) rotates and translates relative to sleeve (204). In particular, seal (212) sealingly engages a smooth portion (254) of a sleeve (250) that is unitarily secured to cutter (50). Sleeve (250) further comprises a hex portion (252).

Other suitable features, components, and configurations for needle (20) and hub (200) will be apparent to those of ordinary skill in the art in view of the teachings herein. For instance, needle (20) and/or hub (200) may be configured in accordance with any of the teachings in U.S. Non-Provisional patent application Ser. No. 12/483,305, entitled "Tetherless Biopsy Device with Reusable Portion," filed Jun. 12, 2009, the disclosure of which is incorporated by reference herein. Still other ways in which needle (20) and/or hub (200) may be formed, including alternative techniques, materials, features, components, configurations, functionalities, and operabilities, will be apparent to those of ordinary skill in the art in view of the teachings herein.

Exemplary Body

As noted above, body (30) of the present example comprises a probe portion (12) and a holster portion (14). In the present example, a battery (not shown), a first circuit board (35), a second circuit board (not shown), a motor (36), and a vacuum pump (38) are provided within probe portion (12). The battery may comprise a rechargeable battery, a non-rechargeable battery (i.e., a battery that is not capable of being recharged), or any other type of battery. In other versions, biopsy device (10) is powered by some other source, such as a conventional alternating current (AC) power source or piece of capital equipment, such that the battery is merely optional. The battery is coupled with motor (36) via first circuit board (35), second circuit board (not shown) and a trigger button (not shown) in the present example. The battery may be similar to the battery disclosed in U.S. Non-Provisional patent application Ser. No. 12/483,305, entitled "Tetherless Biopsy Device with Reusable Portion," filed Jun. 12, 2009, the disclosure of which is incorporated by reference herein.

As shown in FIGS. 3-5, motor (36) of the present example is in mechanical communication with vacuum pump (38) and a cutter actuation mechanism (60). In particular, motor (36) is operable to simultaneously activate vacuum pump (38) and cutter actuation mechanism (60) when motor (36) is activated. Alternatively, vacuum pump (38) and cutter actuation mechanism (60) may be activated in any other suitable fashion. By way of example only, vacuum pump (38) and/or cutter actuation mechanism (60) may be activated manually and/or by separate motors and/or in any other suitable fashion. Motor (36) of the present example comprises a conventional DC motor. However, it should be understood that motor (36) may alternatively comprise a pneumatic motor (e.g., with impeller, etc.), a pneumatic linear actuator, an electromechanical linear actuator, or a variety of other types of movement-inducing devices. Various suitable ways in which other types of movement-inducing devices may be incorporated into biopsy device (10) will be apparent to those of ordinary skill in the art in view of the teachings herein.

As shown in FIGS. 3-5, a drive shaft (62) extends from motor (36), and is rotationally driven by motor (36). A pair of bearings (70) and a drive gear (72) are positioned about drive shaft (62). Bearings (70) support drive shaft (62), while drive gear (72) rotates unitarily with drive shaft (62). In particular, motor (36) may be selectively activated to rotate drive shaft (62) and drive gear (72) in either rotational direction. Drive gear (72) meshes with a second gear (74), which is unitarily secured to a second shaft (64). Second shaft (64) also includes associated bearings (70) and a third gear (76). Second shaft (64) and gears (74, 76) rotate unitarily, such that motor (36) is operable to rotatingly drive second shaft (64) and gears (74, 76) via drive shaft (62) and drive gear (72).

Vacuum pump (38) of the present example comprises a conventional diaphragm pump. In particular, the second shaft (64), which is rotationally driven by motor (36) as described above, is coupled with an eccentric disk (not shown—e.g., a device for converting circular motion into rectilinear motion, comprising a disk fixed off-center to second shaft (64)), which is configured to cause a rod (not shown—e.g., the rod may be coupled with or otherwise driven by the eccentric disk) of vacuum pump (38) to reciprocate as motor (36) and shafts (62, 64) rotate. This rod of vacuum pump (38) drives a diaphragm (not shown) of vacuum pump (38) as the rod reciprocates, causing vacuum pump (38) to induce a vacuum. It should be understood that vacuum pump (38) of the present example operates in the same way regardless of which direction motor (36) rotates. Of course, any other suitable type of vacuum pump may be used. Vacuum pump (38) of the present example is operable to induce a vacuum in tissue sample holder (40) when vacuum pump (38) is activated, as will be described in greater detail below. Cutter actuation mechanism (60) is operable to rotate and translate cutter (50) when cutter actuation mechanism (60) is activated, as will also be described in greater detail below. In particular, cutter actuation mechanism (60) is operable to cause cutter (50) to rotate within first lumen (26) and concomitantly cause cutter (50) to translate within first lumen (26), such as to sever a biopsy sample from tissue protruding through lateral aperture (24).

Other suitable, features, components, and configurations for body (30) and its associated components will be apparent to those of ordinary skill in the art in view of the teachings herein. For instance, body (30) and/or one or more components of body (30) may be configured in accordance with any of the teachings in U.S. Non-Provisional patent application Ser. No. 12/483,305, entitled "Tetherless Biopsy Device with Reusable Portion," filed Jun. 12, 2009, the disclosure of which is incorporated by reference herein. Still other ways in which body (30) and/or its associated components may be formed, including alternative techniques, materials, features, components, configurations, functionalities, and operabilities, will be apparent to those of ordinary skill in the art in view of the teachings herein.

Exemplary Valve Mechanism

As shown in FIGS. 3-6, biopsy device (10) also includes a valve mechanism (150) in the present example. Valve mechanism (150) may be similar to the valve mechanism disclosed in U.S. Non-Provisional patent application Ser. No. 12/483, 305, entitled "Tetherless Biopsy Device with Reusable Portion," filed Jun. 12, 2009, the disclosure of which is incorporated by reference herein. Valve mechanism (150) of this example comprises shuttle valve slider (152), o-rings (210), and sleeve (204) of needle hub (200). Shuttle valve slider (152) is positioned coaxially about cutter (50), and is configured to translate relative to sleeve (204) and relative to cutter (50). Shuttle valve slider (152) defines an inner diameter that is greater than the outer diameter defined by cutter (50), such that a gap is provided between the outer diameter of cutter (50) and the inner diameter of shuttle valve slider (152). Such a gap is sufficient to provide longitudinal fluid communication (e.g., atmospheric air, etc.) between the outer diameter of cutter (50) and the inner diameter of shuttle valve slider (152). In addition, the proximal end of shuttle valve slider (152) has notches (153) formed in it, providing an appearance similar to that of a castellated nut or castle nut.

As shown, stop member (55) and shuttle valve slider (152) are configured such that stop member (55) may push shuttle valve slider (152) proximally when stop member (55) is engaged with shuttle valve slider (152); while sleeve (250) and shuttle valve slider (152) are configured such that sleeve (250) may push shuttle valve slider (152) distally when sleeve (250) is engaged with shuttle valve slider (152). However, the distance between the distal end of sleeve (250) and the proximal end of stop member (55) is greater than the length of shuttle valve slider (152), such that there is a degree of "lost motion" between shuttle valve slider (152) and cutter (50) as cutter (50) translates in the present example. Accordingly, shuttle valve slider (152) and the other components of valve mechanism (150) may be configured to allow shuttle valve slider (152) to selectively substantially seal second lumen (28) relative to openings (208) when cutter (50) is in a proximal position and to selectively vent second lumen (28) to atmosphere when cutter (50) is at other positions.

It should be understood that, as with other components described herein, valve mechanism (150) may be varied, modified, substituted, or supplemented in a variety of ways; and that valve mechanism (150) may have a variety of alternative features, components, configurations, and functionalities. Suitable alternative versions, features, components, configurations, and functionalities of valve mechanism (150) will be apparent to those of ordinary skill in the art in view of the teachings herein. By way of example only, valve mechanism (150) and/or any of its components may be configured in accordance with any of the teachings in U.S. Non-Provisional patent application Ser. No. 12/483,305, entitled "Tetherless Biopsy Device with Reusable Portion," filed Jun. 12, 2009, the disclosure of which is incorporated by reference herein.

Exemplary Tissue Sample Holder

As shown in FIGS. 1-6 (among others), tissue sample holder (40) of the present example comprises a cap (42), an outer cup (44), and a collection tray (46). Tissue sample holder (40) provides a fluid management system that is configured to facilitate separation of tissue samples from associated fluids as will be described in greater detail below. Cup (44) is secured to probe (12) in the present example. Such engagement may be provided in any suitable fashion (e.g., snap fitting, complementary rigid locking features, etc.).

Outer cup (44) of the present example is substantially transparent, allowing the user to view tissue samples on collection tray (46), though outer cup (44) may have any other suitable properties if desired. Collection tray (46) divides the interior space defined by outer cup (44) into an upper chamber (43a) and a lower chamber (43b). As will be described in greater detail below, the fluid management system provided by tissue sample holder (40) is configured to retain tissue samples in upper chamber (43a) while permitting associated fluids to flow into lower chamber (43b).

Outer cup (44) is in fluid communication with cutter lumen (52) and with vacuum pump (38) in the present example. In particular, outer cup (44) is in fluid communication with cutter lumen (52) via a first port (45); and is in fluid communication with vacuum pump (38) via a second port (47). A conduit (39) couples port (41) of vacuum pump (38) with second port (47) of outer cup (44). A spring-loaded seal (not shown) or other feature may optionally be provided on conduit (39) and/or second port (47) and/or port (41) of vacuum pump (38), to substantially seal tissue sample holder (40) and/or vacuum pump (38) when conduit (39) is disconnected from tissue sample holder (40) or vacuum pump (38) and/or when probe (12) is decoupled from holster (14). In the present example, second port (47) is further coupled with a hydrophobic filter (48), which is in fluid communication with the interior space defined by outer cup (44). Hydrophobic filter (48) is configured to permit vacuum pump (38) to induce a vacuum in tissue sample holder (40) while preventing liquids from being communicated from tissue sample holder (40) to vacuum pump (38). In addition to or in lieu of having hydrophobic filter (48) a highly absorbent material may be provided in tissue sample holder (40) to soak up liquids. Alternatively, liquids may be dealt with in any other suitable fashion. As described in greater detail below, the vacuum created in tissue sample holder (40) by vacuum pump (38) is communicated to cutter (50) in the present example. In particular, vacuum pump (38) may thus be used to induce a vacuum in cutter lumen (52); with such a vacuum being communicated through conduit (39), ports (41, 45, 47), and the interior of outer cup (44).

As shown, the interior space defined by outer cup (44) is separated by a collection tray (46) into an upper chamber (43a) and a lower chamber (43b). Collection tray (46) may comprise plastic or any other suitable material or combination of materials. In some versions, collection tray (46) is formed as an integral feature of outer cup (44). In some other versions, collection tray (46) is formed separately from outer cup (44), such that the two are later joined together. In some such versions, collection tray (46) may be removable from outer cup (44) or may remain permanently fixed relative to outer cup (44) after collection tray (46) is joined with outer cup (44). Collection tray (46) of the present example has a tapered configuration, and has a filter opening (147) formed therethrough. In particular, the tapered configuration of collection tray (46) provides ramps leading downwardly toward filter opening (147), such that gravity and the configuration of collection tray (46) leads liquids toward filter opening (147). In some versions, these ramp features are substantially straight. In some other versions, collection tray (46) has a rounded bowl shape, with filter opening (147) being positioned at the bottom center of the bowl shape. Still other suitable configurations for collection tray (46) will be apparent to those of ordinary skill in the art in view of the teachings herein.

In the present example, a flow restriction device (49) is positioned within filter opening (147). Flow restriction device (49) may be configured to selectively control the flow of fluids between upper chamber (43a) and lower chamber (43b). Accordingly, fluids may be collected in lower chamber (43b) and separated from tissue samples retained in upper chamber (43a). Filter opening (147), without flow restriction device (49), may be sized and configured to permit the passage of fluids therethrough while preventing the passage of tissue samples therethrough. Alternatively, filter opening (147) may be sized to permit the passage of tissue samples therethrough, however flow restriction device (49) may be configured to prevent the passage of tissue samples through filter opening (147) when flow restriction device (49) is positioned within filter opening (147).

In the present example, collection tray (46) is positioned below first port (45) which is in fluid communication with cutter lumen (52). Collection tray (46) is thus configured to receive tissue samples and associated fluids that are communicated proximally through cutter (50) as will be described in greater detail below. Collection tray (46) may be sized and shaped to receive a plurality of tissue samples for instances when the user collects multiple samples during a single procedure. In the illustrated version, the surfaces of collection tray (46) are tapered or sloped downward toward filter opening (147) to direct fluids toward filter opening (147) via gravity. It should be understood that collection tray (46) may take a variety of alternate forms. By way of example only, collection tray (46) may comprise a funnel-shape or a convex shape to direct fluids toward filter opening (147). By way of further example only, collection tray (46) may comprise a plurality of filter openings and corresponding flow restriction devices. While filter opening (147) of the present example is a circular opening positioned substantially in the center of collection tray (46), it will be appreciated that filter opening may comprise any shape and location suitable to allow fluids to pass from upper chamber (43a) into lower chamber (43b).

Figure 9:
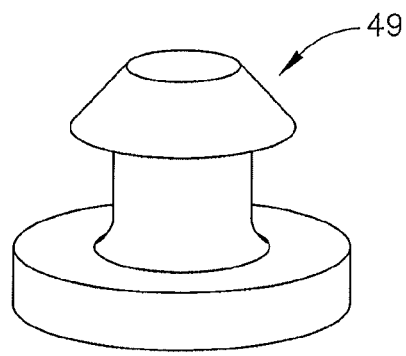
FIG. 9 depicts an exemplary flow restriction device.

FIG. 9 depicts an exemplary flow restriction device (49). Flow restriction device (49) of the present example operates like a check valve, such that it selectively prevents flow of fluids through filter opening (147). In the present example, flow restriction device (49) allows fluids to flow from upper chamber (43a) into lower chamber (43b) while preventing the flow of fluids from lower chamber (43b) into upper chamber (43a). In other words, flow restriction device (49) may be selectively transitioned between an "open configuration" (e.g., such that fluids are permitted to flow from upper chamber (43a) into lower chamber (43b) when upper chamber (43a) is at atmospheric pressure) and a "closed configuration" (e.g., such that fluids are prevented from flowing from lower chamber (43b) into upper chamber (43a) when a vacuum is applied to upper chamber (43a)).

In some versions, flow restriction device may be "vacuum activated" such that flow restriction device (49) transitions from an open position to a closed position when a vacuum is introduced in outer cup (44)/upper chamber (43a). In some such versions, fluids are permitted to flow from upper chamber (43a) into lower chamber (43b) when outer cup (44)/upper chamber (43a) is at atmospheric pressure, while flow restriction device (49) closes or seals filter opening (147) when a vacuum is induced in outer cup (44)/upper chamber (43a) such that fluids are prevented from flowing from lower chamber (43b) into upper chamber (43a). By way of example only, flow restriction device (49) may be formed of a resilient material that deforms under the influence of a vacuum to transition between open and closed configurations. As another merely illustrative example, flow restriction device (49) may include a resilient member (e.g., spring, etc.) that bears against collection tray (46) to resiliently bias flow restriction device (49). In either case, flow restriction device

(49) may be resiliently biased to either the open configuration or the closed configuration, with flow restriction device (49) transitioning to the other configuration based on whether upper chamber (43a) is under a vacuum or atmospheric pressure.

In the present example, flow restriction device (49) "floats" when outer cup (44)/upper chamber (43a) is at atmospheric pressure, such that filter opening (147) remains substantially open, allowing fluids to flow from upper chamber (43a) into lower chamber (43b) and vice-versa. Also in the present example, flow restriction device (49) is drawn toward upper chamber (43a) when a vacuum is induced in outer cup (44)/upper chamber (43a), thereby closing or sealing filter opening (147) and preventing fluids from flowing from lower chamber (43b) into upper chamber (43a) and vice-versa. Flow restriction device (49) may comprise a floating valve seat (as shown in FIG. 9), a vacuum activated check valve, a miniature check valve, a spring-actuated check valve, a duckbill check valve, a wafer check valve, a valve cup assembly (comprising a valve cup and a fitting) or any other device or assembly suitable to selectively control the flow of fluids between upper chamber (43a) and lower chamber (43b). By way of example only, flow restriction device (49) may comprise vacuum fitting part no. HS 18-SV-SS, a valve cup assembly comprising vacuum fitting part no. HS 18-SV-SS and valve cup F77-NBR, a valve cup assembly comprising vacuum fitting part no. HS 18-SV-SS and valve cup F77-SIT, or a 75 Button Valve (part no. 35.50.033), each available from Anver Corporation of Hudson, Mass. In addition, by way of example only, flow restriction device (49) may comprise a duckbill check valve (part no. CKV-M3) available from Beswick Engineering Corp., Inc. of Greenland, N.H., or a Type 369 Wafer Check Valve available from GF Piping Systems of Tustin, Calif. Other suitable forms that flow restriction device (49) may take will be apparent to those of ordinary skill in the art in view of the teachings herein.

Cap (42) is removably coupled with outer cup (44) in the present example. A pair of latches (56) provide selective engagement between cap (42) and outer cup (44). In particular, latches (56) engage a lip (57) of outer cup (44). Lip (57) has gaps (59) permitting passage of latches (56), such that a user may secure cap (42) to outer cup (44) by aligning latches (56) with gaps (59), pushing cap (42) onto outer cup (44), then rotating cap (42) past gaps (59) to engage latches (56) with lip (57). Alternatively, cap (42) may be secured to outer cup (44) in any other suitable fashion. An o-ring (53) provides a seal when cap (42) is engaged with outer cup (44). A vacuum may thus be maintained within outer cup (44) when cap (42) is secured to outer cup (44). In operation, a user may remove cap (42) to access tissue samples that have gathered on collection tray (46) during a biopsy process. In the present example, cap (42) is removed by rotating cap (42) to align latches (56) with gaps (59), then pulling cap (42) off. Of course, cap (42) may be removed from outer cup (44) in any other suitable fashion.

Tissue sample holder (40) of the present example is configured to hold at least ten tissue samples. Alternatively, tissue sample holder (40) may be configured to hold any other suitable number of tissue samples. It should be understood that, as with other components described herein, tissue sample holder (40) may be varied, modified, substituted, or supplemented in a variety of ways; and that tissue sample holder (40) may have a variety of alternative features, components, configurations, and functionalities. For instance, tissue sample holder (40) may be alternatively configured such that it has a plurality of discrete tissue sample compartments that may be selectively indexed to cutter lumen (52). Such indexing may be provided automatically or manually. By way of example only, tissue sample holder (40) may be configured and operable in accordance with the teachings of U.S. Pub. No. 2008/0195066, entitled "Revolving Tissue Sample Holder for Biopsy Device," published Aug. 14, 2008, the disclosure of which is incorporated by reference herein; U.S. Non-Provisional patent application Ser. No. 12/337,997, entitled "Tissue Biopsy Device with Rotatably Linked Thumbwheel and Tissue Sample Holder," filed Dec. 18, 2008; U.S. Non-Provisional patent application Ser. No. 12/337,911, entitled "Biopsy Device with Discrete Tissue Chambers," filed Dec. 18, 2008, the disclosure of which is incorporated by reference herein; or U.S. Non-Provisional patent application Ser. No. 12/337,874, entitled "Mechanical Tissue Sample Holder Indexing Device," filed Dec. 18, 2008, the disclosure of which is incorporated by reference herein. Other suitable alternative versions, features, components, configurations, and functionalities of tissue sample holder (40) will be apparent to those of ordinary skill in the art in view of the teachings herein. Alternatively, tissue sample holder (40) may simply be omitted, if desired.

Figure 10:
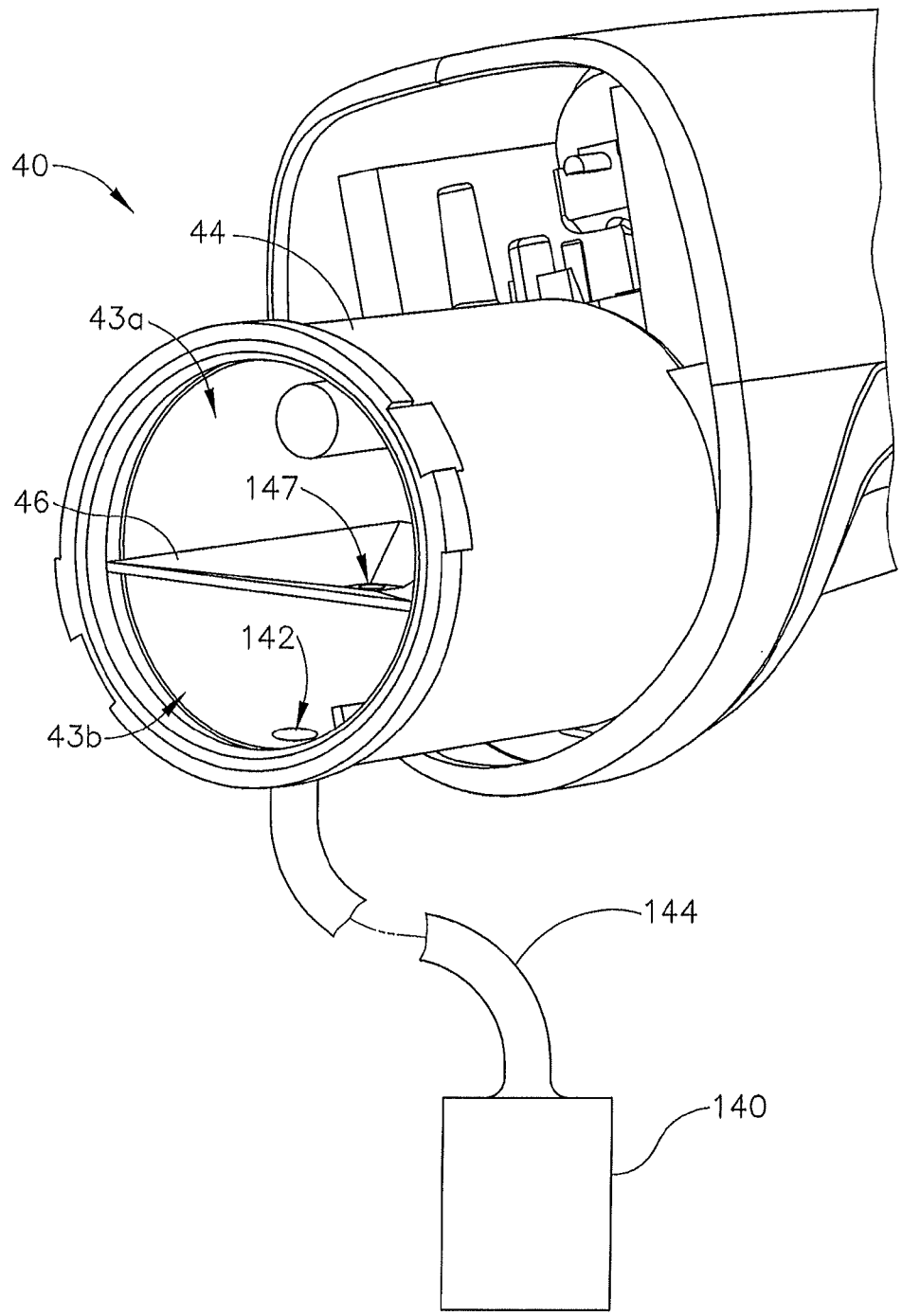
FIG. 10 depicts a partial rear perspective view of an alternate biopsy device and an alternate tissue sample holder, attached to an exemplary fluid retention device.

FIG. 10 depicts an exemplary alternate embodiment in which tissue sample holder (40) is in fluid communication with a fluid container (140) that is located external to biopsy device (10). Specifically, lower chamber (43b) includes a drainage opening (142) in outer cup (44) in this example. Drainage opening (142) is configured to allow fluids collected in lower chamber (43b) to flow out of lower chamber (43b) and into fluid container (140) via tubing (144). Tubing (144) may comprise plastic tubing or any other structure or device suitable to transfer liquids from lower chamber (43b) to fluid container (140). Drainage opening (142) may be suitably shaped, sized, and positioned to efficiently drain fluids from lower chamber (43b). Fluid container (140) may comprise a fluid collection bag, canister, or any other structure or device suitable to receive and collect fluids. Of course, fluid container (140) may be any suitable size and shape. The ability to deposit fluids into fluid container (140) may provide additional flexibility for the user in acquiring multiple samples and managing bleeding because the fluid container (140) may hold more fluids than lower chamber (43b) could otherwise hold by itself. Additionally, the use of fluid container (140) may provide additional flexibility when biopsy device (10) is used in stereotactic or x-ray procedures by reducing the need to directly access tissue sample holder (40) during the procedure to deal with fluids collected during the procedure. Other suitable alternative versions, features, components, configurations, and functionalities of fluid container (140) will be apparent to those of ordinary skill in the art in view of the teachings herein.

Figure 11:
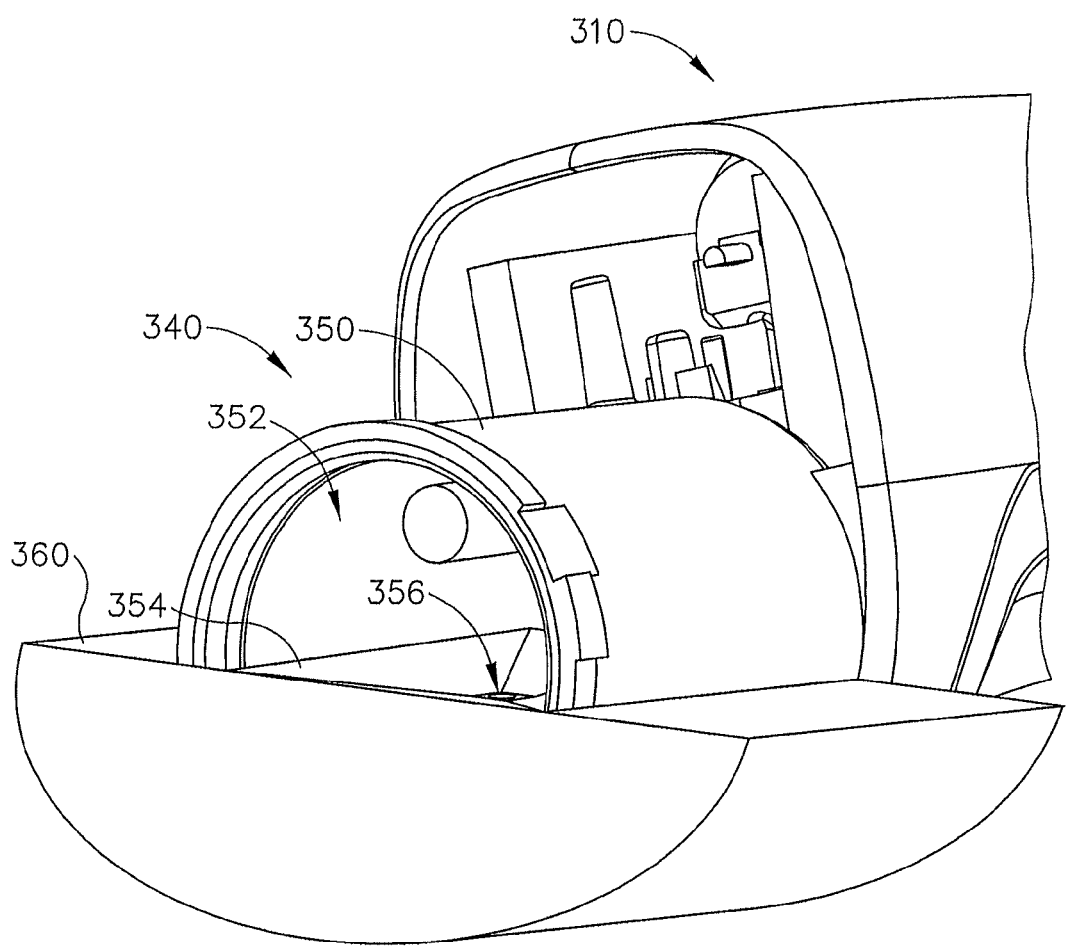
FIG. 11 depicts an alternate tissue sample holder having an enlarged fluid collection chamber, attached to the biopsy device of FIG. 1.

FIG. 11 depicts another exemplary alternate tissue sample holder (340) engaged with a biopsy device (310). The components of biopsy device (310) may be substantially similar to the components of biopsy device (10) described herein, aside from tissue sample holder (340) replacing tissue sample holder (40). In the illustrated version, tissue sample holder (340) comprises an upper portion (350) and a lower portion (360). Upper portion (350) may be releasably or fixedly engaged with lower portion (360). Alternatively, upper portion (350) may be integral with lower portion (360). Upper portion (350) may be substantially similar to the upper portion of outer cup (44) described herein. Similar to upper chamber (43a), upper portion (350) comprises an upper chamber (352) that is in fluid communication with first port (45) and second port (47) of biopsy device (310). Upper chamber (352) further comprises a collection tray (354) that is substantially similar to collection tray (46) described herein. Collection tray (354) is configured to receive tissue samples and associated fluids that are communicated proximally through cutter (50). Collection tray (354) comprises a filter opening (356) similar to filter opening (147) described herein. Collection tray (354) further comprises a flow restriction device (not shown) similar to flow restriction device (49) described herein.

Upper chamber (352) is in selective fluid communication with a fluid collection chamber (not shown) in lower portion (360) via filter opening (356) and the flow restriction device (not shown). The fluid collection chamber in lower portion (360) may be configured to receive and collect fluids from upper chamber (352), just like lower chamber (43b) described above. However, the fluid collection chamber in lower portion (360) in this example may be larger and able to retain a larger amount of fluids compared to lower chamber (43b) described above. The fluid collection chamber in lower portion (360) may have a semi-circular cross-section with a radius that is larger than the radius of upper chamber (352). Of course, any suitable size and shape may be used for lower portion (360) and/or the fluid collection chamber in lower portion (360). In some versions, lower portion (360) may be disengaged from upper portion to allow a user to dispose of fluids stored therein and re-attach lower portion (360) or to replace a first, full lower portion (360) with a second, empty lower portion (360), although this functionality is not required.

The use of lower portion (360) having a larger fluid collection chamber may provide additional flexibility for the user in acquiring multiple samples and managing bleeding because the fluid collection chamber may hold more fluids than lower chamber (43b). Additionally, the use of lower portion (360) having a larger fluid collection chamber may provide additional flexibility when biopsy device (10) is used in stereotactic or x-ray procedures by reducing the need to directly access tissue sample holder (340) during the procedure to deal with fluids collected during the procedure. Other suitable alternative versions, features, components, configurations, and functionalities of lower portion (360) will be apparent to those of ordinary skill in the art in view of the teachings herein.

In some versions, a removable cap (not shown) is provided for upper portion (350), with such a cap being similar to cap (42) described above. Such a cap may take a variety of forms. For instance, such a cap may comprise a semi-circular door that hingedly folds up and down to selectively close or open the proximal side of upper portion (350). Such a door may include a seal on the inside panel of the door and a latch at the top to selectively keep the door substantially closed. As another merely illustrative example, a cap for upper portion (350) may comprise a separate semi-circular piece that selectively clips, latches, or otherwise removably secures to the proximal side of upper portion (350). As yet another merely illustrative example, such a cap may comprise a door that slides up and down vertically, like a tray separator sliding in and out of an organizing tray, to selectively open and close the proximal side of upper portion (350). Other suitable forms that a cap of upper portion (350) may take will be apparent to those of ordinary skill in the art in view of the teachings herein. In some versions where upper portion (350) includes a cap, lower portion (360) is configured such that its proximal side is not open, such that lower portion (360) does not need or otherwise include a removable cap. Alternatively, lower portion (360) may have its own removable cap. Such a removable cap may be similar to or different from a removable cap for upper portion (350).

In some other versions, a single cap (not shown) is used to selectively cover/close or uncover/open the proximal side of both upper portion (350) and lower portion (360). For instance, such a cap may be substantially similar to cap (42) described above, with such a cap having a shape the complements the differing sizes and shapes of upper portion (350) and lower portion (360). Various other suitable ways in which upper portion (350) and lower portion (360) may be selectively covered/closed and/or uncovered/opened will be apparent to those of ordinary skill in the art in view of the teachings herein.

In any of the foregoing examples, tissue sample holder (40, 340) may further comprise a screen or other type of filter above collection tray (46, 354) but below first port (45). Such a screen/filter may be configured to receive tissue samples that are communicated proximally through cutter lumen (52) and first port (45), and keep such tissue samples from reaching filter opening (147, 356) and flow restriction device (49). In other words, such a screen/filter may substantially prevent tissue samples from getting stuck between flow restriction device (49) and collection tray (46, 354), which might otherwise adversely affect the effectiveness of restriction device (49). Such a screen/filter may nevertheless freely permit the passage of fluids therethrough, such that fluids communicated through cutter lumen (52) and first port (45) may still reach filter opening (147, 356) and flow restriction device (49). Such a screen/filter may comprise a conventional screen, a piece of plastic or other material with openings or slots formed therethrough, or any other suitable type of structure, etc. Such a screen/filter may also be removable from tissue sample holder (40, 340), such that the screen/filter may be removed from tissue sample holder (40, 340) first with tissue samples thereon; and then the tissue samples may be removed from the screen/filter after the screen/filter has been removed from tissue sample holder (40, 340). Of course, as with other components described herein, such a screen/filter is merely optional.

Exemplary Cutter

As shown in FIGS. 1-6, cutter (50) of the present example is substantially hollow, such that cutter (50) defines a cutter lumen (52). Cutter (50) also has a substantially sharp distal edge (51), such that cutter (50) is operable to sever a biopsy sample from tissue protruding through lateral aperture (24) of needle (20). Alternatively, the distal end of cutter (50) may have any other suitable configuration. As shown in FIGS. 3-5, a proximal portion of cutter (50) extends into tissue sample holder (40). A vacuum created in tissue sample holder (40) by vacuum pump (38) is thus communicated to cutter lumen (52). A seal (54) is provided at the interface of cutter (50) and outer cup (44). Seal (54) is configured to substantially seal the interface of cutter (50) and outer cup (44), even as cutter (50) rotates and translates relative to outer cup (44). Furthermore, cutter (50) is configured such that it remains in sealed fluid communication with the interior of tissue sample holder (40) even when cutter (50) is in a distal most position. For instance, the length of cutter (50) may be such that at least a portion of cutter (50) is always disposed in outer cup (44) of tissue sample holder (40) during operation of biopsy device (10). Of course, cutter (50) may have any other suitable alternative features or configurations. Similarly, cutter (50) may have any other suitable alternative relationships with tissue sample holder (40).

It should be understood that, as with other components described herein, cutter (50) may be varied, modified, substituted, or supplemented in a variety of ways; and that cutter (50) may have a variety of alternative features, components, configurations, and functionalities. Suitable alternative versions, features, components, configurations, and functionalities of cutter (50) will be apparent to those of ordinary skill in the art in view of the teachings herein. By way of example only, cutter (50) and/or one of its components may be configured in accordance with any of the teachings in U.S. Non-Provisional patent application Ser. No. 12/483,305, entitled "Tetherless Biopsy Device with Reusable Portion," filed Jun. 12, 2009, the disclosure of which is incorporated by reference herein.

Exemplary Cutter Actuation Mechanism

In the present example, cutter actuation mechanism (60) and its components are configured in accordance with the teachings of the cutter actuation mechanism and components disclosed in U.S. Non-Provisional patent application Ser. No. 12/483,305, entitled "Tetherless Biopsy Device with Reusable Portion," filed Jun. 12, 2009, the disclosure of which is incorporated by reference herein. In particular, and as shown in FIGS. 3-5, cutter actuation mechanism (60) of the present example comprises motor (36), shafts (62, 64, 68, 69), gears (72, 74, 76, 78, 80, 82, 84), and bearings (70), each of which are contained within holster (14) in the present example. In particular, gear (72) is rotated by motor (36) which meshes with gear (74) to rotate gear (76) via shaft (64). Gear (76) meshes with gear (78) which rotates gear (80) via shaft (68). Gear (80) meshes with gear (82) which meshes with gear (86) and rotates gear (84) via shaft (69). Gear (84) meshes with gear (88). In the present example, activation of motor (36) will rotate gears (82, 84). As shown in FIG. 2, gears (82, 84) are partially exposed by an opening formed in a cover plate (18) of holster (14) in the present example.

Cutter actuation mechanism (60) of the present example further comprises a hex nut (100) and a worm nut (120). Worm nut (120) is supported by a bushing (138). Hex nut (100) includes a gear (86), which is configured to rotate unitarily with hex nut (100). Worm nut (120) also includes a gear (88), which is configured to rotate unitarily with worm nut (120). Gear (86) is configured to mesh with gear (82) when probe (12) and holster (14) are coupled together; while gear (88) is configured to mesh with gear (84) when probe (12) and holster (14) are coupled together. In particular, and as shown in FIG. 2, gears (86, 88) are partially exposed by an opening formed in a cover plate (16) of probe (12) in the present example. Motor (36) is thus operable to rotatingly drive gears (86, 88) in the present example when probe (12) and holster (14) are coupled together. Such rotation of gears (86, 88) will cause cutter (50) to rotate and translate simultaneously in the present example.

Gear (86) of hex nut (100) is configured to mesh with gear (82), such that rotation of gear (82) causes rotation of hex nut (100). Such rotation of hex nut (100) will cause corresponding rotation of cutter (50). It will therefore be understood that cutter actuation mechanism (60) may cause rotation of cutter (50) in response to activation of motor (36), with rotation of motor (36) being communicated to cutter (50) through shafts (62, 64, 68, 69), gears (72, 74, 76, 78, 80, 82, 84, 86), hex nut (100), and sleeve (250). Of course, any other suitable structures, components, configurations, or techniques may be used to provide rotation of cutter (50).

Gears (82, 84) of holster (14) rotate simultaneously when motor (36) is activated. As noted above, gears (82, 84) mesh with gears (86, 88) of probe (12) when probe (12) is coupled with holster (14), such that activated motor (36) rotates gears (86, 88) simultaneously. Activated motor (36) will thus rotate hex nut (100) and worm nut (120) simultaneously. It should therefore be understood that sleeve (250), cutter (50), lead screw (122), and worm nut (120) will all rotate simultaneously when motor (36) is activated. It will therefore be understood that the simultaneous rotation of sleeve (250), cutter (50), lead screw (122), and worm nut (120) will provide translation of cutter (50) in response to activation of motor (36). Of course, any other suitable structures, components, configurations, or techniques may be used to provide translation of cutter (50).

In the present example, cutter (50) is retracted proximally when motor (36) is activated to rotate cutter (50) counterclockwise (viewed from tissue sample holder (40) toward needle (20)); while cutter (50) is advanced distally when motor (36) is activated to rotate cutter (50) clockwise (viewed from tissue sample holder (40) toward needle (20)). The direction of motor (36) rotation may thus be reversed to transition between distal and proximal translation of cutter (50). Alternatively, cutter actuation mechanism (60) may be configured to be self-reversing, such that cutter (50) may be translated distally and proximally without reversing the direction of motor (36) rotation.

In one merely illustrative example of operation of cutter actuation mechanism (60), cutter (50) may be initially located in a distal-most position, such that lateral aperture (24) is "closed"; with lead screw (122) being positioned at the distal smooth section (137) of worm nut (120). Spring (130) biases lead screw (122) proximally to engage threads (132) with threads (134). At this stage, clockwise rotation of cutter (50) relative to worm nut (120) will not result in any translation of cutter (50) (e.g., lead screw (122) will essentially "freewheel"); while counterclockwise rotation of cutter (50) relative to worm nut (120) will result in proximal translation of cutter (50). As cutter (50) is rotated by motor (36) and cutter actuation mechanism (60) in the counterclockwise direction (viewed from tissue sample holder (40) toward needle (20)), cutter actuation mechanism (60) causes cutter (50) to retract proximally. As noted above, such proximal or rearward translation may be effected through engagement of threads (132, 134), and due to lead screw (122) rotating at a faster speed than worm nut (120). Lead screw (122) continues to traverse threads (134) of worm nut (120) as cutter (50) continues to retract proximally.

Cutter (50) then reaches a proximal-most position, such that lateral aperture (24) is "opened". At this stage, lead screw (122) is positioned at the proximal smooth section (136) of worm nut (120). Spring (128) biases lead screw (122) distally to engage threads (132) with threads (134). At this stage, continued counterclockwise rotation of cutter (50) relative to worm nut (120) will not result in any translation of cutter (50) (e.g., lead screw (122) will essentially "freewheel"); while clockwise rotation of cutter (50) relative to worm nut (120) will result in distal translation of cutter (50). To that end, motor (36) may again be activated, with its rotation direction being reversed to reverse the rotation direction of cutter (50) and associated components. In particular, reversing the rotational direction of motor (36) causes cutter (50) to rotate clockwise (viewed from tissue sample holder (40) toward needle (20)). Such clockwise rotation of cutter (50) causes cutter to advance distally to reach the distal-most position again.

While cutter (50) is shown and described above as rotating counterclockwise (viewed from tissue sample holder (40) toward needle (20)) during retraction of cutter (50) and clockwise (viewed from tissue sample holder (40) toward needle (20)) during advancement of cutter (50), it should be immediately apparent to those of ordinary skill in the art that cutter (50) may instead be rotated clockwise during retraction of cutter (50) and counterclockwise during advancement of cutter. For instance, such reversal may be provided by reversing the orientation of threads (132, 134). Alternatively, such reversal may be provided by changing the differential such that worm nut (120) rotates faster than cutter (50). Of course, any other suitable structures, components, configurations, or techniques may be used to provide translation and/or rotation of cutter (50). It should therefore be understood that, as with other components described herein, cutter actuation mechanism (60) may be varied, modified, substituted, or supplemented in a variety of ways; and that cutter actuation mechanism (60) may have a variety of alternative features, components, configurations, and functionalities. By way of example only, biopsy device (10) may be configured such that cutter (50) does not translate (e.g., such that cutter (50) merely rotates, etc.); or such that cutter (50) does not rotate (e.g., such that cutter (50) merely translates, etc.). Other suitable alternative versions, features, components, configurations, and functionalities of cutter actuation mechanism (60) will be apparent to those of ordinary skill in the art in view of the teachings herein.

Exemplary Pneumatic Operation

As noted above, vacuum pump (38) is operable to induce a vacuum in tissue sample holder (40), and such vacuum may be further communicated to cutter lumen (52). Specifically, vacuum pump (38) may induce a vacuum in upper chamber (43*a*) of tissue sample holder (40) which may cause flow restriction device (49) to close thereby preventing fluids from passing from lower chamber (43*b*) to upper chamber (43*a*). In particular, vacuum pump (38) may start building a vacuum in cutter lumen (52) as soon as motor (36) is activated; and such a vacuum may continue to build or be maintained as cutter (50) starts moving proximally toward the retracted position. At this stage, second lumen (28) is vented to atmosphere. In particular, shuttle valve slider (152) is in a distal position, allowing atmospheric air to reach second lumen (28)—via openings (208), notches (153), the gap between the inner diameter of shuttle valve slider (152) and the outer diameter of cutter (50), and the portion of sleeve interior (206) that is distal to shuttle valve slider (152). Alternatively, second lumen (28) may be fluidly coupled with vacuum pump (38), such that a vacuum is created in second lumen (28) at this stage.

As cutter (50) moves toward the retracted position, such that lateral aperture (24) of needle (20) is "partially open," a vacuum in cutter lumen (52) may be further communicated through first lumen (26), which may draw tissue into lateral aperture (24). At this stage, second lumen (28) is still vented to atmosphere. In particular, due to the "lost motion" between cutter (50) and shuttle valve slider (152), shuttle valve slider (152) remains in the distal position despite proximal retraction of cutter (50). Alternatively, second lumen (28) may be fluidly coupled with vacuum pump (38), such that a vacuum is created in second lumen (28) at this stage.

When cutter (50) reaches the fully retracted position, such that lateral aperture (24) of needle (20) is "open", a vacuum in cutter lumen (52) may continue to be further communicated through first lumen (26), which may continue to draw tissue into lateral aperture (24). Of course, some amount of tissue may naturally prolapse into lateral aperture (24) without the assistance of vacuum, such that vacuum may not even be needed to draw tissue into lateral aperture (24). At this stage, second lumen (28) is substantially sealed relative to atmosphere. In particular, stop member (55) has pushed shuttle valve slider (152) to a proximal position, such that o-rings (210) "straddle" openings (208) and seal against the interior sidewall of sleeve portion (204) to prevent atmospheric air from being communicated from openings (208) to second lumen (28) via hollow interior (206) of sleeve portion (204). In addition, while cutter (50) is at the fully retracted position, motor (36) may continue to operate to run vacuum pump (38). For instance, motor (36) may run vacuum pump (38) for anywhere between approximately 0.5 seconds (inclusive) and approximately 4 seconds (inclusive), or for any other suitable duration, while cutter (50) remains in the fully retracted position. During this time, cutter (50) may "freewheel" (e.g., rotate in place without also translating). Such continued activation of vacuum pump (38) may substantially maintain/ achieve a vacuum in tissue sample holder (40).

As motor (36) is reversed and cutter (50) is advanced to sever tissue protruding through lateral aperture (24), vacuum pump (38) may continue to induce a vacuum in cutter lumen (52), and second lumen (28) may eventually be vented to atmosphere. However, in the initial stages of advancement of cutter (50) from the proximal-most position to the distal-most position, the "lost motion" between cutter (50) and shuttle valve slider (152) leaves shuttle valve slider (152) in the proximal position until cutter (50) advances far enough for the distal end of sleeve (250) to engage the proximal end of shuttle valve slider (152). Until such engagement between the distal end of sleeve (250) and the proximal end of shuttle valve slider (152), o-rings (210) of shuttle valve slider (152) continue to substantially seal second lumen (28) from openings (208). After the distal end of sleeve (250) engages the proximal end of shuttle valve slider (152), and after cutter (50) has continued to move distally to a sufficient degree, the distal end of sleeve (250) eventually pushes shuttle valve slider (152) distally, such that the proximal-most o-ring (210) is eventually moved distal to openings (208). With shuttle valve slider (152) reaching such a position (and positions that are further distal to such a position), second lumen (28) is again vented to atmosphere as described above. As cutter (50) again finally reaches the distal-most position, cutter (50) may completely sever the tissue protruding through lateral aperture (24), with second lumen (28) being vented.

With the severed tissue sample residing in cutter lumen (52), with vacuum pump (38) drawing a vacuum at the proximal face of the severed tissue sample, and with the venting being provided at the distal face of the severed tissue sample (via openings (208), second lumen (28), and openings (27)), the pressure differential applied to the severed tissue sample may cause the severed tissue sample to be drawn proximally through cutter lumen (52) and into upper chamber (43*a*) of tissue sample holder (40). The severed tissue sample may thus be deposited on collection tray (46) of tissue sample holder (40); or on a screen positioned above collection tray (46) in tissue sample holder (40). Any fluids drawn through cutter lumen (52) into upper chamber (43*a*) of tissue sample holder (40) may flow through filter opening (147) into lower chamber (43*b*). In some versions, this flow of fluids from upper chamber (43*a*) to lower chamber (43*b*) occurs while a vacuum is being applied to upper chamber (43*a*) via second port (47). In some such versions, while flow restriction device (49) permits fluid to flow from upper chamber (43*a*) to lower chamber (43*b*) while upper chamber (43*a*) is under a vacuum, flow restriction device (49) does not permit fluid to flow from lower chamber (43*b*) to upper chamber (43*a*). In some other versions (e.g., where flow restriction device (49) remains closed under the influence of a vacuum, etc.), this flow of fluids from upper chamber (43*a*) to lower chamber (43*b*) does not occur until upper chamber (43*a*) returns to atmospheric pressure. In some such versions, while flow restriction device (49) permits fluid to flow from upper chamber (43*a*) to lower chamber (43*b*) while upper chamber (43*a*) is at atmospheric pressure, flow restriction device (49) does not permit fluid to flow from lower chamber (43*b*) to upper chamber (43*a*).

Of course, any other suitable structures, components, configurations, or techniques may be used to provide selective sealing and/or venting of second lumen (28). By way of example only, while shuttle valve slider (152) is actuated mechanically based on the axial position of cutter (50) in the present example, it should be understood that shuttle valve slider (152) or any other type of valve may instead be actuated electrically (e.g., via a separate motor or solenoid), pneumatically, or otherwise. Furthermore, in some variations of biopsy device (10), a vacuum, saline, pressurized air, atmospheric air, and/or any other medium may be communicated to second lumen (28) at any suitable stage of operation of biopsy device (10) (e.g., applying vacuum or venting to second lumen (28) during and/or upon retraction of cutter (50) and/or during advancement of cutter (50), sealing second lumen during advancement of cutter (50), etc.). Suitable alternative structures, components, configurations, or techniques for communicating severed tissue samples proximally through cutter lumen (52) to reach tissue sample holder (40) will be apparent to those of ordinary skill in the art in view of the teachings herein.

Exemplary Method of Operation

In a merely exemplary use of biopsy device (10), a user first inserts tissue piercing tip (22) into the breast of a patient. During such insertion, cutter (50) may be advanced to the distal-most position, such that lateral aperture (24) of needle (20) is closed. As also noted herein, such insertion may be performed under visual guidance, stereotactic guidance, ultrasound guidance, MRI guidance, PEM guidance, BSGI guidance, palpatory guidance, some other type of guidance, or otherwise. With needle (20) sufficiently inserted into the patient's breast, the user may then activate motor (36), which may in turn activate vacuum pump (38) and cutter actuation mechanism (100). Such activation of vacuum pump (38) may induce a vacuum in tissue sample holder (40) and cutter lumen (52) as described above. Such activation of cutter actuation mechanism (60) may cause cutter (50) to rotate counterclockwise and translate proximally. As cutter (50) starts retracting and when cutter (50) reaches the retracted position, vacuum from vacuum pump (38) (as communicated through tissue sample holder (40) and cutter lumen (52)) may draw tissue into lateral aperture (24) of needle (20). During this time, second lumen (28) may be vented by valve mechanism (150).

Once cutter (50) reaches a proximal-most position, vacuum may still be communicated through vacuum lumen (52) and first lumen (26), drawing tissue into lateral aperture (24) of needle (20). Second lumen (28) may be substantially sealed by valve assembly (150) at this time. In addition, lead screw (122) freewheels yet is biased distally by spring (128) as cutter (50) continues to rotate counterclockwise. Lateral aperture (24) is fully open at this stage, with tissue prolapsed therein.

The rotation direction of motor (36) is then reversed and cutter (50) begins to advance distally until again reaching the distal-most position. As cutter (50) advances distally, vacuum is still being communicated through vacuum lumen (52), helping to hold tissue in place as sharp distal edge (51) of cutter (50) begins to sever the tissue. Second lumen (28) is initially substantially sealed by valve assembly (150) at this time, but is eventually vented. Cutter (50) then reaches the distal-most position, thereby "closing" lateral aperture (24), and such that sharp distal edge (51) of cutter (50) completely severs the tissue. Vacuum is still being communicated through cutter lumen (52) at this time, and valve assembly (150) vents second lumen (28). As described above, this combination of vacuum and venting provides communication of the severed tissue sample proximally through cutter lumen (52) and onto collection tray (46) of tissue sample holder (40). Motor (36) may continue to operate at the end of the cutting stroke, thereby continuing to drive vacuum pump (38) to maintain a vacuum in tissue sample holder (40). In addition, spring (130) biases lead screw (122) proximally to engage threads (132), while allowing cutter (50) to continue rotating at the distal-most position. A cutting stroke will thus be complete, and may be initiated as many times as desired to acquire additional tissue samples.

Fluids communicated onto collection tray (46) during a cutting stroke may drain via gravity through filter opening (147) into lower chamber (43*b*) when upper chamber (43*a*) is at atmospheric pressure. Fluids captured in lower chamber (43*b*) may be prevented from flowing back into upper chamber (43*a*) by flow restriction device (49). Flow restriction device (49) may be selectively transitioned between an "open position" (i.e. when fluids are permitted to flow from upper chamber (43*a*) into lower chamber (43*b*)) and a "closed position" (i.e. when fluids are prevented from flowing from lower chamber (43*b*) into upper chamber (43*a*)) in response to a vacuum being induced or maintained within upper chamber (43*a*). For instance, when outer cup (44)/upper chamber (43*a*) is at atmospheric pressure, flow restriction device (49) may permit fluids to flow from upper chamber (43*a*) into lower chamber (43*b*) and vice-versa. When a vacuum is induced in outer cup (44)/upper chamber (43*a*), flow restriction device (49) may prevent fluids from flowing from upper chamber (43*a*) into lower chamber (43*b*) and vice-versa.

As noted above, several cutting strokes may be performed to acquire several tissue samples without the user having to withdraw needle (20) from the patient's breast. The user may adjust the orientation of lateral aperture (24) about the axis defined by needle (20) by rotating the entire biopsy device (10) between cutting strokes for multiple sample acquisition. Alternatively, biopsy device (10) may be configured such that needle (20) is rotatable relative to body (30), such that needle (20) may be rotated via a thumbwheel or other feature. Once the desired number of tissue samples have been obtained, the user may withdraw needle (20) from the patient's breast. The user may then remove cap (42) from cup (44) and retrieve the tissue samples from collection tray (46).

At the end of a procedure, the user may separate probe (12) from holster (14). Holster (14) may then be cleaned and/or sterilized for subsequent use. Probe (12) may be disposed of. Alternatively, as noted above, biopsy device (10) may alternatively be formed as a unitary construction, such that there is no probe (12) separable from a holster (14).

Of course, the above examples of use of biopsy device (10) are merely illustrative. Other suitable ways in which biopsy device (10) may be used will be apparent to those of ordinary skill in the art in view of the teachings herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A tissue sample holder for a biopsy device, the tissue sample holder comprising:
    (a) a hollow outer cup;
    (b) a collection tray positioned within the outer cup, wherein the collection tray and hollow outer cup together define an upper chamber and a lower chamber, wherein the collection tray includes an opening; and
    (c) a flow restriction device disposed within the opening of the collection tray, wherein the flow restriction device is operably configured to selectively seal the opening in response to a vacuum being induced within the upper chamber.

2. The tissue sample holder of claim 1, wherein the flow restriction device comprises a resilient material, wherein the resilient material is configured to resiliently bias the flow restriction device to permit fluid flow through the opening of the collection tray.

3. The tissue sample holder of claim 1, wherein the flow restriction device is selected from the group consisting of a floating valve seat, a vacuum activated check valve, a miniature check valve, a spring-actuated check valve, a duckbill check valve, a wafer check valve, and a valve cup assembly.

4. The tissue sample holder of claim 1, wherein the collection tray is tapered towards the opening in the collection tray.

5. The tissue sample holder of claim 1, wherein the collection tray is funnel-shaped.

6. The tissue sample holder of claim 1, wherein the opening is centered within the collection tray.

7. The tissue sample holder of claim 1, wherein the collection tray is configured to receive a plurality of tissue samples.

8. The tissue sample holder of claim 1, wherein the collection tray is integral with the outer cup.

9. The tissue sample holder of claim 1 further comprising an external fluid container in fluid communication with the lower chamber via a drainage opening formed in the outer cup.

10. The tissue sample holder of claim 1, wherein the upper chamber has a semi-circular cross-section defined by a first radius, wherein the lower chamber has a semi-circular cross-section defined by a second radius, wherein the second radius of the lower chamber is substantially larger than the first radius of the upper chamber.

11. A tissue sample holder for a biopsy device, the tissue sample holder comprising:
    (a) a multi-chamber cup, wherein the multi-chamber cup comprises a first chamber and a second chamber, wherein the first chamber is in selective fluid communication with the second chamber; and
    (b) a flow restriction device, wherein the flow restriction device is positioned between the first chamber and the second chamber, wherein the flow restriction device is operable to selectively transition between a closed state and an open state in response to application of a vacuum to the first chamber.

12. The tissue sample holder of claim 11, further comprising a collection tray, wherein the collection tray is positioned between the first chamber and the second chamber.

13. The tissue sample holder of claim 12, wherein the collection tray defines an opening, wherein the flow restriction device is positioned within the opening.

14. The tissue sample holder of claim 11, wherein the multi-chamber cup further comprises a first port and a second port, wherein the first port is in fluid communication with the first chamber, wherein the second port is in fluid communication with the first chamber.

15. The tissue sample holder of claim 14, wherein the first port is configured to communicate a tissue sample into the first chamber.

16. The tissue sample holder of claim 14, wherein the second port is in communication with a vacuum pump, wherein the vacuum pump is configured to induce and maintain a vacuum within the first chamber.

17. A tissue sample holder for a biopsy device comprising:
    (a) an outer cup, wherein the outer cup defines a hollow interior divided into a first chamber and a second chamber;
    (b) a first port, wherein the first port is in communication with the first chamber;
    (c) a second port, wherein the second port is in communication with the first chamber, wherein the second port is configured to induce a vacuum in the first chamber;
    (d) a collection tray positioned between the first chamber and the second chamber, wherein the collection tray is adjacent to the first port;
    (e) a flow restriction device positioned within an opening in the collection tray, wherein the flow restriction device is configured to selectively transition between an open configuration and a closed configuration, wherein the flow restriction device is configured to maintain the open configuration when the first chamber is at atmospheric pressure.

18. The tissue sample holder of claim 17, wherein the flow restriction device is further configured to allow fluid flow from the first chamber into the second chamber in the open configuration, wherein the flow restriction device is further configured to prevent fluid from flowing from the second chamber into the first chamber in the closed configuration.

19. The tissue sample holder of claim 17, wherein the flow restriction device is configured to maintain the closed configuration when a vacuum is maintained in the first chamber.

20. The tissue sample holder of claim 17, wherein the flow restriction device is configured to transition between the open configuration and the closed configuration in response to a change in the amount of pressure present in the first chamber.

* * * * *